United States Patent [19]

Yang et al.

[11] Patent Number: 4,666,855
[45] Date of Patent: May 19, 1987

[54] RAPID METHOD FOR DETERMINING THE ISOELECTRIC POINT FOR AMPHOTERIC MOLECULES

[75] Inventors: Victor C. Yang, Cambridge; Robert S. Langer, Somerville, both of Mass.

[73] Assignee: Massachusetts Institute of Technology, Cambridge, Mass.

[21] Appl. No.: 761,114

[22] Filed: Jul. 31, 1985

[51] Int. Cl.[4] .................. C12Q 1/00; G01N 33/68
[52] U.S. Cl. .................. 436/89; 204/182.6; 435/4; 436/163; 436/164
[58] Field of Search ............ 436/86, 89, 71, 163, 436/164; 204/182.6; 435/4

[56] References Cited

U.S. PATENT DOCUMENTS 4,110,077 8/1978 Klein et al. ................. 436/71
4,139,440 2/1979 Chrambach et al. ........ 436/86
4,356,072 10/1982 Saito e al. .................. 204/182.6

OTHER PUBLICATIONS

CA-80:45592z-Sandulesca.
Svensson, ACTA Chem. Scand. vol. 15, (1961), No. 2, pp. 325-341.
Svensson, ACTA Chem. Scand. vol. 15, (1962), pp. 456-466.
Svensson, Archives of Biochemistry and Biophysics, Supplement 1, (1962), pp. 132-138.
Vesterberg et al., ACTA Chem. Scand. vol. 20, (1966), pp. 820-834.
Sluyterman et al., Journal of Chromatography, vol 150(1978), pp. 31-44.
Righetti et al., Journal of Chromatography, vol. 127 (1976), pp. 1-28.
Righetti et al., Journal of Chromatography, vol. 220 (1981), pp. 115-194.
Malamud et al., Analytical Biochemistry, vol. 86 (1978), pp. 620-647.
Horuk et al., FEBS Letters, vol. 155, No. 2 (1983), pp. 213-217.
Lan et al., Archives of Biochemistry and Biophysics, vol. 200, No. 1, (1980), pp. 206-215.
Righetti et al., Biochimica et Biophysica Acta, vol. 532 (1978), pp. 137-146.
Shinjo et al., FEBS Letters, vol. 105 (1979), No. 2, pp. 353-356.
Lampson et al., Anal. Biochem, vol. 11(1965) pp. 374-377.

Primary Examiner—Michael S. Marcus
Attorney, Agent, or Firm—Paul J. Cook

[57] ABSTRACT

A rapid method for determining the isoelectric point for an amphoteric molecule of interest is provided which utilizes the pH-dependent binding affinity of the molecule for an ion-exchange material. The empirically derived pI values are within a range of 0.2 pH units or less of the reported values in the literature and may be more precisely determined by employing a narrower pH gradient as part of the procedure. The unique methodology allows isoelectric point determinations to be accomplished within one hour's time, avoids carrier ampholyte interaction or artifact formation, and allows the determination to be performed at any desired temperature with decreased risk of denaturation.

7 Claims, 10 Drawing Figures

RAPID METHOD FOR DETERMINING THE ISOELECTRIC POINT FOR AMPHOTERIC MOLECULES

The Government has rights in this invention pursuant to Grant Number NIH-5-R01-GM25810-06 awarded by the National Institutes of Health.

FIELD OF THE INVENTION

The present invention is concerned generally with isolation and purification methods for amphoteric molecules such as proteins and is specifically directed to rapid methods for determining isoelectric points of amphoteric molecules accurately and precisely.

BACKGROUND OF THE INVENTION

The isoelectric point (hereinafter "pI") is an important parameter which is useful in determining the acid-base properties of amphoteric molecules such as proteins and polypeptides. The pI is generally defined as the pH value at which the net overall charge on the molecule is zero. A knowledge of the pI for a particular amphoteric substance, therefore, aids the investigator in selecting between the ever increasing number of protein isolation techniques to obtain and purify an amphoteric molecule of interest. Some of the better known isolation techniques include isoelectric focusing, chromatofocusing, isoelectric precipitation, disc electrophoresis, isotachophoresis, ion-exchange chromatography and ammonium sulfate fractionation. In particular, with the advent of isoelectric focusing and chromatofocusing, pI data for proteins and polypeptides have been accumulated and enlarged such that more than 1,000 of protein pI values have been determined over the past two decades [Righetti et al., *J. Chromatogr.* 127:1–28 (1976); Righetti et al., *J. Chromatogr.* 220:116–194 (1981); Malamud et al., *Anal. Biochem.* 86:620–647 (1978)].

Despite the need for useful pI data to aid in the use of the above-identified protein isolation techniques, the present methods for generally determining pI such as isoelectric focusing or chromatography present several drawbacks. One is the excessively long processing time required to utilize these methods. Another is the effect of the processing time on the accuracy and precision of the method itself; for example, when isoelectric focusing is used, the isoelectric point (as measured by the pH at which a protein zone is found) varies as a function of the electrofocusing time during a transient phase of indeterminant length [Horuk et al., *FEBLETT.* 155:213–217 (1983); An Der Lan et al., *Arch. Biochem. Biophys.* 200:206–215 (1980)]. This period of electrofocusing time must be measured for each individual protein under test before any accurate pI value can be determined. A third drawback is that pI determinations obtained by presently known methods are usually limited by a strict requirement that they be performed at 4° C.; the 4° C. environment is maintained in order to lessen the risk of protein denaturation resulting from either the long focusing times or the high electric field involved. The difficulty arises because the pI value of a protein depends upon the dissociation constants (pK) of the ionizable amino acids present and is, therefore, temperature dependent; accordingly, a pI value obtained at 4° C. is not necessarily accurate or indicative of the true pI value for that protein at any other temperature. A fourth deficiency is that unless a gel containing immobilized carrier ampholytes is used as part of the methodology, the presence of carrier ampholytes in the medium can interact with the proteins under test and cause the formation of complexes and artifacts [Righetti et al., *Biochem. Biophys. Acta.* 532:137–146 (1978); Gianazza et al., in *Electrophoresis* (Radola, B. J., Ed.) Vol. 79, 1980, pp 129–140; Shinjo et al., *FEBS Letters* 105:353–356 (1979)].

Alternative methods for determining the isoelectric point for amphoteric molecules have been investigated. Of these, the report of Lampson and Tytell [*Anal. Biochem.* 11:374–377 (1965)] that the pI of a protein could be determined by CM-Sephadex column chromatography using buffers with increasing pH as an eluent is the most pertinent. The Lampson and Tytell technique has several inherent deficiencies: the method requires multiple chromatographic procedures and is very time consuming; by the nature of the ion-exchange material used by the investigators, the method is limited for use to only those proteins having an isoelectric point above pH 6.0; in addition, deviations of 0.4–0.6 pH units from the literature values for each of the proteins tested was empirically obtained using this method. For these reasons, there remains an apparent and longstanding need for methods to determine the isoelectric point of proteins, polypeptides and other molecules which is simple to perform, rapid in processing time, provides accuracy and reproductibility with a minimum deviation of results and is both versatile and available to amphoteric molecules in general without limitation.

SUMMARY OF THE INVENTION

A novel, rapid method for determining the isoelectric point for an amphoteric molecule of interest is provided which comprises the steps of: preparing a plurality of test solutions at varying pH values, each test solution comprising the amphoteric molecule of interest in buffer containing low ionic strength, preparing a plurality of test suspensions at varying pH values, each test suspension comprising an ion-exchange material and the same low ionic strength buffer described above; combining each of the test solutions with a test suspension having a substantially identical pH value as a series of reaction mixtures, whereby, at least a portion of the amphoteric molecules becomes bound to the ion-exchange material in each of the reaction mixtures; and determining the quantity of amphoteric molecules remaining unbound in each reaction mixture as a function of pH value, the pH value at which the largest proportional change in binding occurs being the isoelectric point for the amphoteric molecule of interest. This novel method allows isoelectric measurements to be achieved within one hour's duration and avoids any possible carrier ampholyte interaction or artifact formation. In addition, the isoelectric points of proteins and polypeptides can be measured at any desired temperature without substantial risk or denaturation with assurance that the empirically obtained pI were both accurate and reproducible.

DETAILED DESCRIPTION OF THE DRAWINGS

The present invention may be more fully and completely understood when taken in conjunction with the accompanying drawing, in which.

DETAILED DESCRIPTION OF THE PREFERRED EMBODIMENTS

Figure 1:
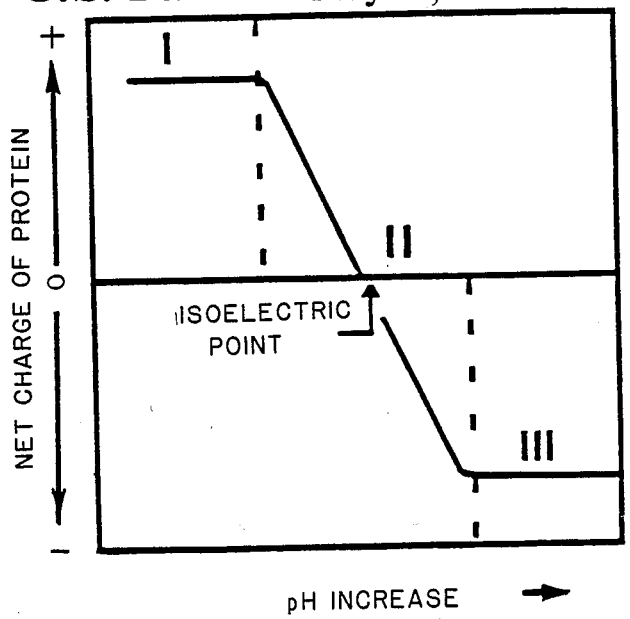
FIG. 1 is a graph illustrating the change in overall net electrical charge of a protein as a function of pH.

The present invention is a simple, facile method for determining isoelectric points and may be applied universally to any type of amphoteric molecule or substance. The method is feasible to determine pI values for not only proteins, with and without enzymatic activity, for polypeptides, but also for any other type of amphoteric molecules including polymers, dyes, polyionic substances and pure amphoteric compounds for which no adequate assays to measure isoelectric points are now available. For these reasons, although the bulk of the illustrative examples are well characterized and defined proteins, it will be expressly understood that the invention is suitable for amphoteric molecules in general without limitations.

The present novel method for determining pI for an amphoteric molecule of interest is based upon and takes advantage of the pH-dependent binding affinity of amphoteric molecules for an ion-exchange material. Using proteins as the representative example of substances whose pI may be determined using the present invention, it is generally recognized and accepted that all proteins, whether or not they possess enzymatic activity, demonstrate the characteristic property that their net overall electrical charge is dependent upon the pH in the surrounding environment. The change in overall electrical charge is demonstrated by FIG. 1 which illustrates a typical pH-charge profile as an anti-sigmoid curve composed of three distinctive regions. In regions I and III, the protein molecule is saturated in positive charge and negative charge respectively; its net charge becomes essentially independent of the pH value in each of these regions. Within region II, the overall net charge decreases with the increase of pH until it reaches a zero value, at which the pH is termed "the isoelectric point" of the protein. With further increases of pH, the overall net charge then becomes more and more negative. Due to this pH-dependent charge characteristic, all proteins, being composed of ionizable groups, demonstrate a pH-dependent binding affinity for ion-exchange materials—the degree of affinity varying with the pH value. The rapid and accurate determination of pI values for proteins (and other amphoteric molecules) using the present invention is thus based upon such discriminating affinity binding behavior.

The present methodology, therefore, is a pH-dependent binding analysis which is performed in four successive steps: preparation of a series of test solutions in a variety of pH values, each of which contains the protein of interest in known concentration; preparation of a series of test suspensions at a variety of pH values, each suspension containing an ion-exchange material such as SP-Sephadex C-50 or QAE-Sephadex A-50 in known quantity; combining each test solution containing the protein of interest with a test suspension containing ion-exchange material as a reaction mixture, the test solution and the test suspension having substantially identical pH values individually; and determining the quantity of protein which remains unbound in each of these reaction mixtures as a function of the pH values over the entire pH range tested, the pH values at which the largest proportional change in affinity binding for the protein occurs being the isoelectric point for the protein of interest. This methodology overcomes all the deficiencies of techniques known in the prior art and offers several distinct and important advantages. First, it allows the pI value to be determined within a time period as short as one hour. Second, because of the short processing time required, the pI determinations may be performed at any desired temperature without substantial risk of denaturation. Third, it avoids the possibility of artifact formation or carrier ampholyte interaction which is often encountered using conventional methods. Fourth, it provides the opportunity to measure the pI value of an amphoteric molecule in any type of buffer system. This novel methodology is also effective to resolve and identify the individual pI values for proteins and other amphoteric substances which have the property of microheterogeneity (i.e., the protein exists in various isomeric forms with slightly different isoelectric points)—if each individual isoelectric point differs from the other by at least 1 pH unit. To demonstrate each of these advantages and because the methodology may be performed in alternative modes, each of the individual steps will be described individually.

Preparation of the Test Solution

Proteins whose concentration may be monitored by following optical adsorbance at 280 nanometers (hereinafter "nm") were prepared in distilled water to a concentration of 4.0 milligrams per milliliter (hereinafter "mg/ml"). Proteins such as beef insulin (greater than 99% pure) was purchased from Elanco, Inc.; bovine serum albumin (98%–99% pure), horse myoglobin (horse skeletal muscle 95%–100% pure), β-lactoglobulin B (from bovine milk, single band by disc gel electrophoresis), carbonic anhydrase B (from bovine erythrocytes, 2500 W-A units/mg) were purchased from Sigma Corporation. Heparinase was isolated from *Flavobacterium heparinum* and purified by hydroxylaptite chromatography [Yang et al., *J. Biol. Chem.* 260:1849–1857 (1985)]. Horse ferritin which demonstrates a much higher extinction coefficient at 280 nm than these other proteins was prepared at a concentration of 0.8 mg/ml. Other proteins which are normally assayed by their enzymatic activities were prepared at a slightly lower concentration ranging from 0.2 to 2 mg/ml owing to the high activities of the enzymes and a high sensitivity of the present assay method. Carbonic anhydrase and heparinase are preferably prepared at a concentration of 0.4 and 1.6 mg/ml respectively. Protein solutions of each appropriate concentration were prepared as 1.0 ml aliquots and were added to a series of test tubes containing 1.0 ml of 40 mM phosphate buffer having an increasing pH increment of 0.1–0.4 pH units. The protein aliquots after mixing with the phosphate buffer were commonly identified as "buffered protein solutions" since their pH values remained within 0.1 pH units of the pH values in the original phosphate buffers alone.

Preparation of the Test Suspensions

The preferred ion-exchange material for use in preparing the test suspensions is SP-Sephadex C-50 or QAE-Sephadex A-50. While these comprised the preferred ion-exchange materials, a wide variety of other resins, cationic and/or anionic, may be usefully employed. These include the following: Dowex-1-Chloride, Dowex-2-Chloride, Dowex-50-Hydrogen, Dowex HCR-5, Dowex HCR-W2, Dowex WGR-2, Dowex SBR, Amberlite IRA, IRP, CG and IRC, DEAE-Sephadex, CM-Sephadex and any QAE-, DEAE-, SP-, CM-Sepharose or cellulose derivatives.

The preferred methodology utilizes 400 mg of SP-Sephadex C-50 (or QAE-Sephadex A-50) which were previously swollen in 40 ml of distilled water overnight. After being swollen and gentle mixing, aliquots containing 1.0 ml of the gel suspension were transferred into small graduate centrifuged tubes and combined with equal volumes (1.0 ml) of 40 mM phosphate buffer prepared at varying pH values corresponding to those for the buffered protein solutions previously prepared. After a short period of mixing and equilibration of about 3 minutes duration, the gel suspension was centrifuged at 20× gravity for 3 minutes and the supernatant removed using conventional methods. The gel was then washed three tixes using individual 10 ml volumes of phosphate buffer, each having a pH value identical to that previously used for equilibration, but being half-diluted in concentration (i.e., diluted 1:1 v/v with distilled water) in order to match the ionic strength of the individual pH variant gels. Since ion-exchange materials per se possess weak buffering power, in some instances additional washings with phosphate buffer at the appropriate pH may be required in order to properly equilibrate the gel suspension to the desired pH value; this is especially true for those gel suspensions at pH values greater than 8.0 or less than 5.0 which are beyond the buffering capacity of the 40 mM phosphate buffer. After the last washing, each aliquot of gel suspension was brought to a final volume of 1.0 ml by addition of the phosphate buffer used for washing the subtile gel particles.

Combination of the Test Solutions and Test Suspensions

Each gel suspension aliquot having a known pH value was then combined with an equal volume of the buffered protein solution having a substantially identical pH value as a reaction mixture. In this manner, a series of test solutions are combined individually with test suspensions at substantially identical pH values, each reaction mixture representing a different pH value. The entire pH range, approximately from 3 to 9, is thus represented by the entire series of reaction mixtures as a whole. Although binding between the protein molecules and the gel suspensions takes place instantaneously in each reaction mixture, the protein-gel mixture is preferably incubated with occasional and gentle mixing for 5-10 minutes to assure completion of the adsorption. The temperature at which this affinity binding occurs is of no importance so long as the temperature is maintained consistently throughout the entirety of the analysis. After this short incubation period, the reaction mixture was centrifuged at 2000× gravity for three minutes followed by removal of the supernatant using conventional methods. The supernatant was then buffered to pH 7 by addition of an equal volume of 0.4 M sodium phosphate buffer (pH 7.0), mixed and then assayed for protein concentration by optical absorbance at 280 nm or by measurement of its enzymatic activity. It will be recognized that the supernatant fluid contains that quantity of protein which remains unbound and non-adsorbed to the ion-exchange material at the individual pH value for that reaction mixture. However, because the extinction coefficient, biological activity and stability of proteins are recognized as being pH dependent, it is essential to bring the pH of each supernatant obtained from the individual reaction mixtures present at various pH values for purposes of ion-exchange absorption to the same pH value before any determination for protein concentration is carried out. This is preferably achieved as described above, by adding aliquots of concentrated buffer having a high buffering capacity (0.4 M sodium phosphate, pH 7) to each individual supernatant fluid prior to analysis. For this reason, the term "analysis solution" is commonly used to identify the supernatant fluid obtained after the protein-gel suspension adsorption.

In order to facilitate the use of the methodology comprising the present invention, a simplified table containing the conditions in detailed procedures for a representative analysis is included as Table I below.

TABLE I

| | |
|---|---|
| I. | PREPARATION OF THE BUFFERED PROTEIN SOLUTIONS |
| a[1]. | The protein was dissolved in distilled water (1–4 mg/ml). |
| b. | Aliquots (1 ml) of protein solution were added to a series of test tubes containing 1 ml of 40 mM phosphate buffer with an increasing increment of 0.1–0.4 pH unit. |
| II. | PREPARATION OF THE BUFFERED GEL SUSPENSIONS |
| a. | 400 mg of ion-exchanger (AQE-Sephadex A-50 or SP-Sephadex C-50) were swollen in 40 mM of distilled water overnight. |
| b. | Aliquots (1 ml) of the suspended gels were transferred into small graduated Falcon polystyrene centrifuge tubes containing 1 ml of 40 mM phosphate buffer at pH's used in (I)b. |
| c. | After 3 minutes of equilibration, the gel suspension was centrifuged at 2,000 g for 3 minutes with a Damon DPR-6000 centrifuge and the supernatant was removed. |
| d. | The beads were washed with 20 mM phosphate buffer at pH's used in (II)b and the supernatant was removed as described in (II)c. |
| e. | Step (II)d was repeated for 2–3 times. |
| f. | After the last wash, each sample was brought up to a total volume of 1 ml by adding buffer onto the settled gel particles. |
| III. | BINDING ANALYSIS |
| a[2]. | 1 ml of the sample in (I)b was added to the sample in (II)f at the same pH. |
| b. | The sample was incubated with occasional and gentle vortexing for 5–10 minutes. |
| c. | Supernatant was removed by centrifugation at 2,000 g for 3 minutes. |
| d[3]. | One volume of the supernatant was buffered to pH 7 by adding one volume of 0.4 M phosphate buffer (pH 7), and then assayed. |
| IV. | DETERMINATION AND CALCULATION OF THE ISOELECTRIC POINT |
| a. | The absorbance (Y axis) was plotted versus pH (X axis). |
| b. | Data points which construct the inflection area were best fitted by a least-squares program (Y = mX + b), and the m and b values were computed. |
| c. | The pI value was calculated by using the following equation: |

$$pI = \frac{1}{m}\left[\left(\frac{Y_H + Y_L}{2}\right) - b\right]$$

where $Y_H$ and $Y_L$ are the Y values (absorbance) of higher plateau and the lower plateau, respectively, of the Absorbance-pH plot.

[1] The amount of protein used depends upon the sensitivity of the assay method used.
[2] In general, a protein/resin (uM/g) ratio of 70 is used.
[3] For proteins whose assays are affected by the presence of high ionic strength, this step is replaced by a modified procedure described in the text.

Although determination of isoelectric points using this binding analysis methodology may not be necessarily compromised by an incomplete adsorption of protein (or amphoteric molecules), it is recommended that an excess amount of ion-exchange material be used in preparing the test suspensions. The amount of protein used in preparing the test solutions is preferably 1/10 or less of the total available adsorption capacity value, as estimated by the manufacturer on the basis of moles of hemoglobin bound per mg of gel suspension (*Ion Exchange Chromatography: Principles and Methods,* Pharmicia Fine Chemicals, Uppsala, Sweden, 1983, pp. 13-16). In general, it is preferred that strong ion-exchange materials such as SP-Sephadex and QAE-Sephadex be used in preparing the test suspensions rather than weak ion-exchange materials such as DEAE-Sephadex and CM-Sephadex, because the adsorption capacities of strong ion-exchange materials are constant over a much wider range of pH values than the weak ones.

In addition, for some proteins, or amphoteric molecules in general, whose enzymatic properties or biological activities are affected by liquids of high ionic strength, the "buffering" step adjusting each supernatant fluid to pH 7.0 as described above is inappropriate. To determine the isoelectric point for proteins such as these, an alternative methodology is used to perform the pH-dependent binding analysis by simultaneously employing both cationic and anionic exchange materials prepared at varying pH values under identical conditions. The ratio of unbound proteins remaining in the supernatant of each individual reaction mixture, the analysis solution, after adsorption with cationic exchange material is compared to that quantity of protein which remains non-adsorbed after reaction with an anionic exchange material is calculated and determined graphically as a function of varying pH values. This ratio of remaining unadsorbed protein (cationic:anionic) can thus be prepared as a profile in relation to the individual pH values. For ratios greater than 1, the reciprocal of them should be used. By this method, the pH value corresponding to a ratio of 1.0 would, therefore, be the true isoelectric point for the protein. This alternative methodology insures that no buffering of any reactant would occur in these procedures; in addition, other inadvertant errors which might be created by the pH and effects would also be eliminated as a consequence of using cationic and anionic exchange materials. This alternative method will be described in greater detail in the examples which follow.

Specific examples of isoelectric point determinations for well known and characterized proteins in alternative modes follow. It will be expressly understood, however, that the proteins used for analysis are merely working illustrations of the methodology in general and that the invention is not restricted in any way to these specific examples alone. To the contrary, the methodology comprising the present invention is useful for determinations of isoelectric points for amphoteric molecules in general and in no instance is deemed to be limited to any specific application.

EXAMPLE I

To illustrate the methodology comprising the present invention, proteins with well defined isoelectric points which are commonly used as pI markers and other assays were tested. For those proteins which were monitored by a non-specific method (absorbance at 280 nm), a protein purity of over 95% was chosen to eliminate errors caused by inadvertent contamination by other protein substances. However, for those proteins which were evaluated using a specific enzymatic assay, the purity of the protein under test is no longer as critical and, in fact, crude preparations may be utilized without loss of accuracy or precision.

Beef insulin, bovine serum albumin, horse myoglobin, bovine carbonic anhydrase, bovine $\beta$-lactoglobulin were prepared as a series of test solutions at varying pH values and combined with SP-Sephadex at varying pH values as a series of test suspensions. Similarly, horse myoglobin, horse ferritin and heparinase were prepared as test solutions and combined with test suspensions of QAE-Sephadex. After combination into individual reaction mixtures and isolation of the individual analysis solutions, the concentration of non-adsorbed proteins were monitored by optical absorbance at 280 nm using conventionally known equipment. Heparinase activity was measured by the increase in ultraviolet absorption at 232 nm [Linker et al., *Biochemistry* 11:563-568 (1972)], according to the procedures of Linhardt et al., [*Biochem. Biophys. Acta.* 702:192-203 (1982)]. Carbonic anhydrase activity was measured spectrophotometrically following the method of Anrmstrong et al., [*J. Biol. Chem.* 241:5137-5149 (1966)], using p-nitrophenyl acetate as a substrate. The adsorbance was then measured at 348 nm and the observed enzymatic rates corrected for the rate of ester hydrolysis in the absence of enzyme.

The results of the binding analysis for each of these proteins is given in FIGS. 2a-2g which show the pH-dependent adsorption profiles for each of the proteins examined. The data points for each profile were best fitted by curves following a least-squares procedure; for the least-squares analysis, that set of data points leading to the smaller standard deviation is used. The arrow within FIGS. 2a-2g indicates the isoelectric point for each protein tested.

Depending upon the kind of ion-exchange material used (SP-Sephadex or QAE-Sephadex), each adsorption profile is either an analog or a mirror image of the profile seen in FIG. 1. As can be seen in FIGS. 2a-2g generally, two plateaus are seen in each curve profile. The higher plateau represents the pH range where the protein molecules carry a charge of the same polarity as that of the ion-exchange material and thus remain unbound within the reaction mixture. The lower plateau represents the region where the protein molecules are totally bound, adsorbed to the ion-exchange material. The inflection between the plateaus corresponds to region II of FIG. 1 and represents the change of the binding affinity of the protein due to the change of its overall electrical charge characteristics. The midpoint of a transition is taken to be the isoelectric point for the protein where there is no overall net charge on the molecule.

A summary of the determined isoelectric points taken from the profiles of FIGS. 2a-2g together with the pH values for these proteins as reported in the literature is summarized by Table II.

TABLE II

| Protein Tested | pH-Dependent Binding Analysis | | Reported Isoelectric Point |
|---|---|---|---|
| | Ion-Exchanger | Temp | pI Values* | pI Values at 4° C. or 25° C. |
| $\beta$-lactoglobulin (bovine milk) | SP | 25 | 5.25 ± 0.03 | 5.31 |

TABLE II-continued

| Protein Tested | pH-Dependent Binding Analysis | | Reported Isoelectric Point | |
|---|---|---|---|---|
| | Ion-Exchanger | Temp | pI Values* | pI Values at 4° C. or 25° C. |
| Insulin (beef) | SP | 25 | 5.40 ± 0.05 | 5.32 |
| Myoglobulin[a] (horse skeletal muscle) | QAE | 25 | 7.15 ± 0.05 | 7.33–6.88 |
| Ferritin[a] (horse spleen) | QAE | 25 | 4.45 ± 0.05 | 4.50–4.23 |
| Carbonic Anhydrase B (bovine erythrocytes) | SP | 4 | 6.30 ± 0.04 | 6.18 |
| Albumin[a] (bovine serum) | SP | 4 | 5.20 ± 0.03 | 5.18–4.98 |
| Heparinase (F. heparinum) | QAE | 4 | 8.42 ± 0.06 | 8.50 |

[a] Proteins have the property of microheterogeneity and show more than one pI value.
*pI values are determined in 20 mM phosphate buffer.

Although the pI values empirically derived using the present methodology could have been measured at any desired temperature, they were in fact determined either at 4° C. or 25° C. in order to be compared appropriately with the literature pI values. It will be noted that in every instance the empirically derived pI value was within 0.2 pH units or less of the previously reported value in the literature regardless of what type of ion-exchange material (cationic or anionic) was used. If desired, more precise pI values may be empirically obtained by preparing test solutions and test suspensions having individual pH values which form a pH gradient differing by a much narrower pH increment than 0.1–0.4 pH units. Since the pI value of a protein is dependent upon the ionic strength and the buffer system used, it is important to recognize that the pI values in Table II described above are measured using 20mM phosphate buffer.

It will be also recognized that the methodology used to obtain the data of FIGS. 2a–2g and Table II utilized a "buffering" adjustment which brought the pH of each supernatant fluid obtained to a single, constant pH value of 7.0 before the determination for non-absorbed protein was carried out. In each instance, this was achieved by adding aliquots of concentrated buffer, 0.4M phosphate buffer, to each individual analysis solution. The amount of buffer added in each instance was identical.

EXAMPLE II

As an example of those proteins whose enzymatic properties or biological activities are affected by liquids of high ionic strength, heparinase was isolated from *Flavobacterium heparinum* and purified by hydroxylaptite chromatography following the method of Yang et al., *J. Biol. Chem.* 260:1849–1857 (1985). The hydroxylapatite-purified heparinase was dialyzed against distilled water overnight to be essentially salt free, lyophilized and then stored at −20° C. until required. To prepare the heparinase as a series of test solutions, 2 mg of lyophilized hydroyxlapatite-purified heparinase was combined with 1 ml of 20 mM phosphate buffer at increasing pH increments of 0.2–0.4 units to cover a pH range from 6.3 to 9.8. Similarly, test suspensions (1 ml) using SP-Sephadex C-50 as a cationic exchange material and QAE-Sephadex A-50 as the anionic exchange material was prepared at varying pH values from 6.3 to 9.8 in 20 mM phosphate buffer. The test solutions were then combined individually with the test suspensions at substantially identical pH values. After the isolation of the individual analysis solutions by conventional methods, the concentrations of the nonadsorbed heparinase were measured by the increase in ultraviolet adsorption at 232 nm [Linker et al. *Biochemistry* 11:563–568 (1972)], according to the procedures of Linhardt et al. [*Biochem. Biophys. Acta.* 702:192–203 (1982)].

Figure 3:
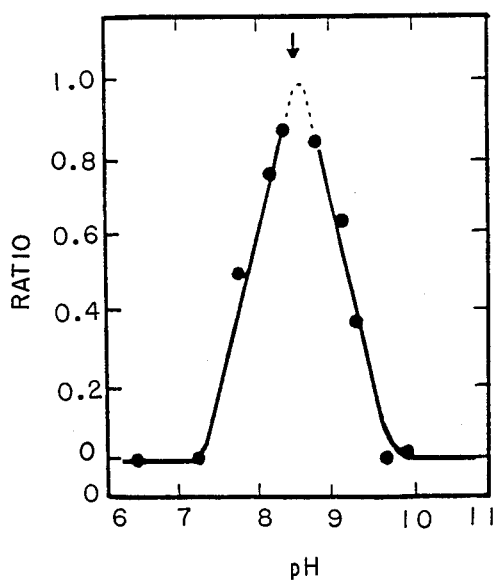
FIG. 3 is a graph illustrating the pH-binding ratio profile useful for estimating the isoelectric point of heparinase.

The results of the non-adsorbed heparinase as a cationic:anionic ion exchange ratio in relation to changes of pH is shown in FIG. 3. The isoelectric point (the 1:1 ratio point) was determined to be pH 8.5 from the extrapolated profile. This value is in excellent agreement with that obtained from the literature by chromatofocusing [Yang et al., *J. Biol. Chem.* 260: 1849–1857 (1985)] and isoelectric focusing [Langer et al., in *Biomaterial: Interfacial Phenomenon and Applications, Advances in Chemistry Series*, American Chemical Society, Washington, D.C., 1982, p. 493–509].

EXAMPLE III

The method comprising the present invention is also effective in resolving individual pI values of a protein which exists in various isometric forms with slightly different isoelectric points—if each isoelectric point for that protein differs from the other by at least 1 pH unit. This technique is demonstrated by preparation of a crude cell extract from *Flavobacterium heparinum* following the method of Yang et al., [*J. Biol. Chem.* 260:1849–1857 (1985)]. Although the extract is far from a pure, homogeneous preparation, it contains two enzymes, heparinase and heparitinase, which act on heparin as a common substrate [Linker et al., *Methods Enzymol.* 28:902–911 (1972)]. For this reason, this crude cell extract is similar in characteristic to a single protein possessing microheterogeneity. The crude extract was prepared as a series of test solutions containing a protein concentration of 8 mg/ml in 20 mM phosphate buffer at increasing pH increments of 0.2–0.4 units to cover a pH range from 6.3 to 10. Similarily, test suspensions of QAE-Sephadex A-50 were prepared at varing pH values from 6.3 to 10 in 20 mM phosphate buffer. One ml of test solutions was then combined with 1 ml of test suspensions at substantially identical pH values. After the isolation of the individual analysis solutions by the conventional method, the activities of the non-adsorbed heparinase and heparitinase or heparin were measured by the increase in ultraviolet adsorption at 232 nm [Linker et al., *Biochemistry* 11:563–568 (1972)], according to the procedures of Linhardt et al., [*Biochim. Biophys. Acta* 602:192–203 (1982)].

Figure 4:
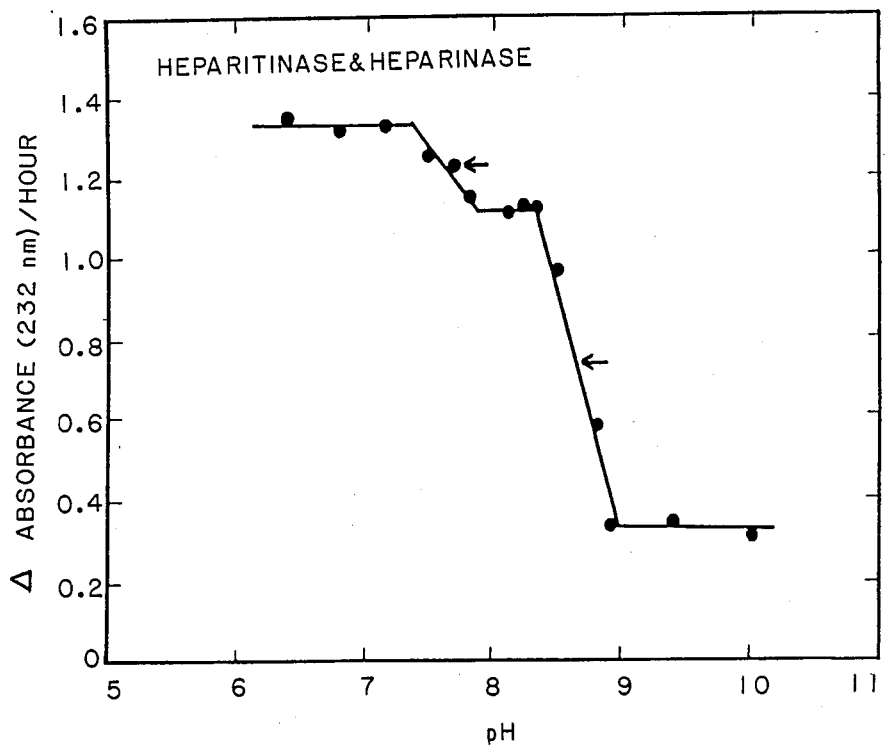
FIG. 4 is a graph illustrating the pH-dependent adsorption profile of the crude cell extract obtained from *Flavobacterium heparinum*.
Figure 2A:
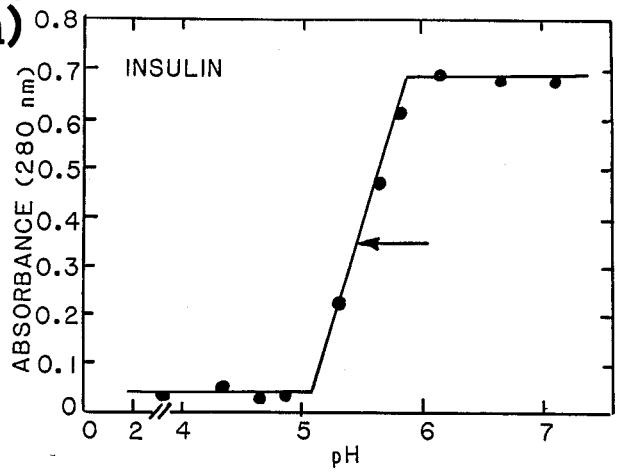
FIGS. 2a–2g are graphs individually illustrating the pH-dependent adsorption profiles for beef insulin, bovine serum albumen, horse myoglobin, bovine carbonic anhydrase, horse ferritin, bovine β-lactoglobulin and Flavobacterial derived heparinase respectively.
Figure 2B:
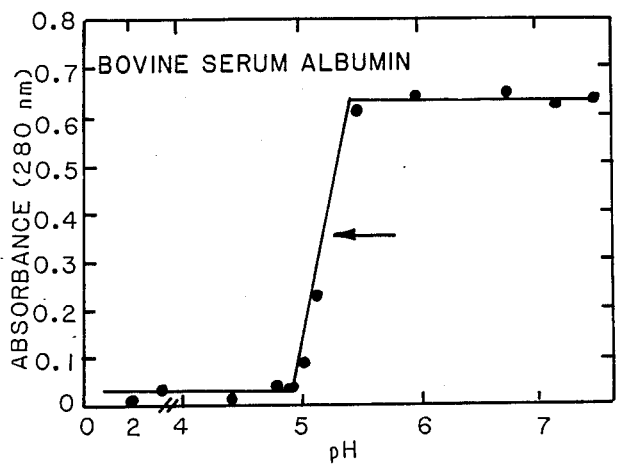
Figure 2C:
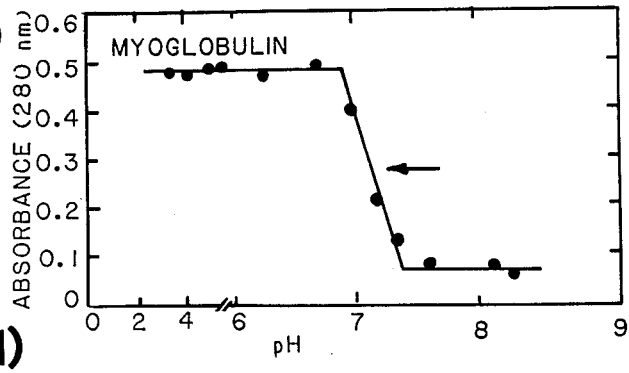
Figure 2D:
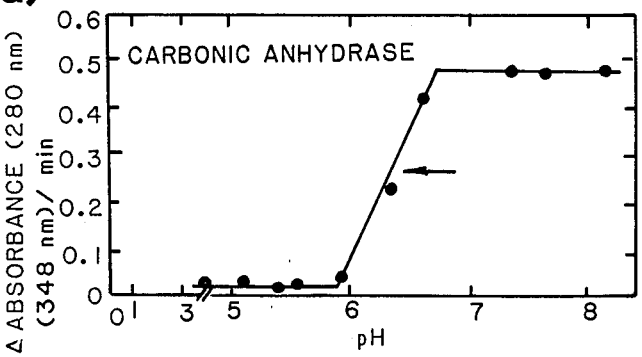
Figure 2E:
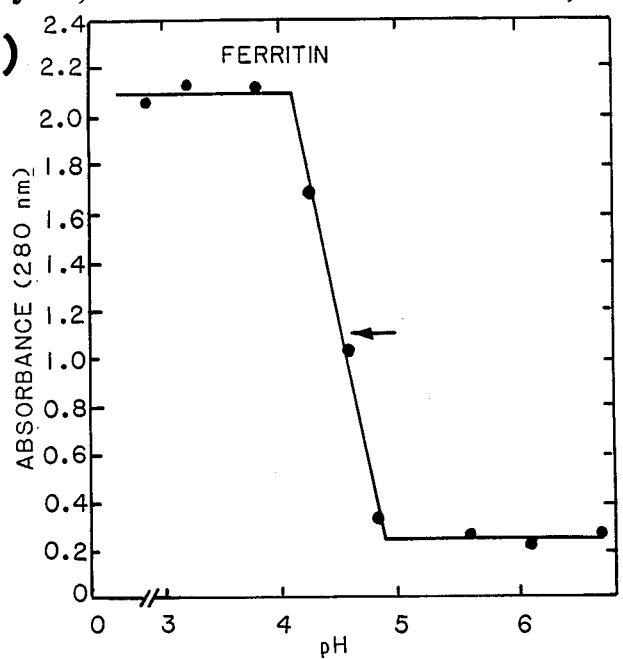
Figure 2F:
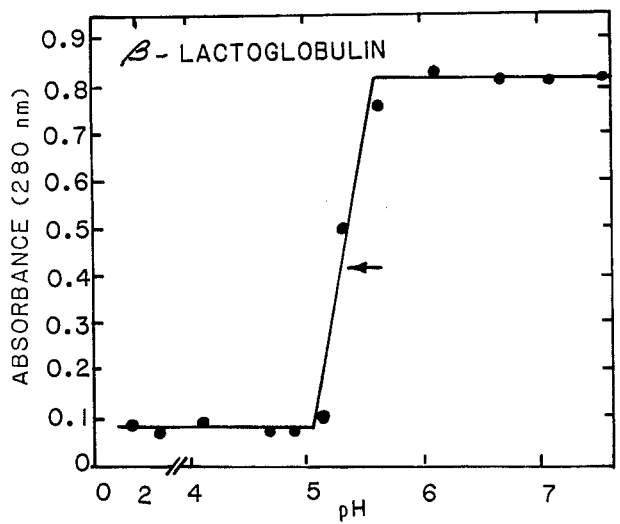
Figure 2G:
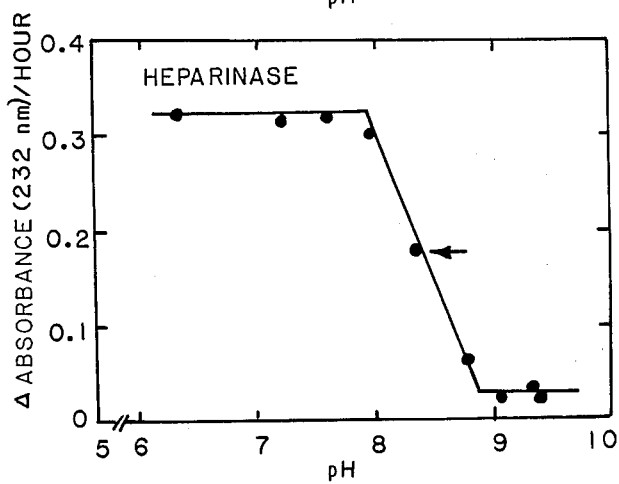

The empirically derived results are given in FIG. 4 as a pH-adsorption profile which contains three plateau regions which are joined by two separate inflections. The appropriate pI values were determined by identifying the pH value at the mid point of each inflection; these were pH 7.7 and pH 8.7, respectively—isoelectric points which are consistent with literature values for heparitinase [Yang et al., *Carbohydra. Res.* (1985)] and heparinase [Yang et al., *J. Biol. Chem.* 260:1849–1856 (1985)]. Thus, a protein with two isoelectric points that differ by at least one pH unit may be resolved using this method. Note however, that with isoelectric points having a difference of less than 1 pH unit, the two inflections may not be wide enough apart to yield a third plateau existing between the higher and lower ones. In such instances, only one inflection covering a broad range of pH values would be observed and no accurate or individual pI values would be obtained. It is specifically for this reason that the requirement of having one pH unit difference between the pI values is made.

It is apparent, therefore, that the method comprising the present invention regardless of mode of use, offers simplicity of procedure, a short processing time, usually less than one hour's duration, accuracy with a deviation of less than 0.2 pH units and a versatility and availability to specific applications and needs unlike any other procedure now available. For these reasons, the invention is not to be restricted in scope nor limited in form except by the claims appended hereto.

We claim:

1. A method for determining the isoelectric point for an amphoteric molecule comprising the steps of:
    preparing a plurality of test solutions at varying pH values, each said test solution comprising the amphoteric molecule;
    preparing a plurality of test suspensions at varying pH values, each said test suspension comprising an ion-exchange material;
    combining each of said test solutions with a test suspension having a substantially identical pH value as a series of reaction mixtures for a period of time to assure completion of adsorption of the amphoteric molecule by the ion-exchange material, whereby at least a portion of the amphoteric molecule becomes bound to said ion-exchange material in each of said reaction mixtures; and
    determining the quantity of amphoteric molecule remaining unbound in each reaction mixture as a function of pH value, the pH value at which the largest proportional change in binding occurs being the isoelectric point for the amphoteric molecule.

2. The method as recited in claim 1, wherein said determination of unbound amphoteric molecule as a function of pH value further comprises:
    separating each of said reaction mixtures into a supernatant and a sediment;
    adjusting the pH of each said supernatant to a preselected pH value; and
    measuring the optical absorbance of said pH adjusted supernatant at a preselected wavelength, said optical absorbance serving to quantify the amount of unbound amphoteric molecule in each of said reaction mixtures.

3. The method as recited in claim 2, wherein each of said supernatants is adjusted to pH 7.0.

4. The method as recited in claim 1, wherein said ion-exchange material is a cationic ion-exchanger.

5. The method as recited in claim 1 wherein said ion-exchange material is an anionic ion-exchanger.

6. The method as recited in claim 1 wherein said determination of unbound amphoteric molecule further comprises determining the ratio of said unbound amphoteric molecule using a cationic exchange material in comparison to an anionic ion-exchange material.

7. The method as recited in claim 1 wherein a plurality of isoelectric points for an amphoteric molecule are determined.

* * * * *